United States Patent
Lisner et al.

(10) Patent No.: US 9,625,391 B2
(45) Date of Patent: Apr. 18, 2017

(54) LIBS MEASUREMENT TUBE

(71) Applicant: K+S AKTIENGESELLSCHAFT, Kassel (DE)

(72) Inventors: Udo-Walter Lisner, Moers (DE); Torsten Rest, Heringen (DE); Jessica Waechter, Eschwege (DE); Joachim Makowe, Aachen (DE); Volker Moerkens, Huertgenwald (DE); Christoph Dominic Gehlen, Aachen (DE)

(73) Assignee: K+S Aktiengesellschaft, Kassel (DE)

( * ) Notice: Subject to any disclaimer, the term of this patent is extended or adjusted under 35 U.S.C. 154(b) by 0 days.

(21) Appl. No.: 14/898,025

(22) PCT Filed: Jun. 12, 2014

(86) PCT No.: PCT/DE2014/000300
§ 371 (c)(1),
(2) Date: Mar. 11, 2016

(87) PCT Pub. No.: WO2014/198256
PCT Pub. Date: Dec. 18, 2014

(65) Prior Publication Data
US 2016/0187260 A1 Jun. 30, 2016

(30) Foreign Application Priority Data
Jun. 14, 2013 (DE) .................. 10 2013 009 962

(51) Int. Cl.
*G01J 3/30* (2006.01)
*G01N 21/71* (2006.01)
(Continued)

(52) U.S. Cl.
CPC .......... *G01N 21/718* (2013.01); *G01J 3/0291* (2013.01); *G01J 3/443* (2013.01);
(Continued)

(58) Field of Classification Search
CPC ............ G01N 21/718; G01N 21/8507; G01N 21/645; G01N 2201/06113; G01N 2201/8592; G01J 3/01; G01J 3/44
See application file for complete search history.

(56) References Cited

U.S. PATENT DOCUMENTS 5,452,070 A 9/1995 Mochizuki et al.
5,453,832 A 9/1995 Joyce
(Continued)

FOREIGN PATENT DOCUMENTS

DE 44 43 407 A1 6/1995
DE 103 59 447 B4 3/2006
(Continued)

OTHER PUBLICATIONS

International Search Report issued Oct. 17, 2014 in PCT/DE2014/000300 (with English language translation).

*Primary Examiner* — Abdullahi Nur
(74) *Attorney, Agent, or Firm* — Oblon, McClelland, Maier & Neustadt, L.L.P.

(57) ABSTRACT

(EN) The invention relates to a special LIBS measurement tube focusing unit, referred to simply as LIBS measurement tube, for vertically dipping into a material to be analyzed, which material is moved in a horizontal flow, characterized in that the measurement tube extends vertically and is internally hollow and open at least at the bottom end, such that a bottom edge is formed at the bottom end, the measurement tube has an inlet for coupling in a laser beam and an outlet for coupling out an emission spectrum at the upper end, the measurement tube is constructed in such a way that, in the measurement tube, the laser beam is focused at the material to be analyzed, specifically bulk material, in particular raw, intermediate, and end products from the processing of potash, magnesium, rock salt, or evaporated salt, but without additional scattering and deflection occurring, (Continued)

such that a plasma of the material to be analyzed is produced within the measurement tube by the laser radiation and the emission spectrum of the material to be analyzed reaches the outlet for outcoupling through the interior of the measurement tube, and scrapers (1, 2) lie on the inner and outer focusing tube wall annularly, preferably at the same vertical height on the focusing tube (3), which scrapers are arranged in such a way that the scrapers can be moved vertically in relation to the focusing tube (3), such that material to be analyzed that adheres to the focusing tube (3) on the inside and outside in the lower region can be scraped off by a relative motion of the focusing tube (3) in relation to the scrapers (1, 2).

20 Claims, 3 Drawing Sheets

(51) Int. Cl.
*G01J 3/443* (2006.01)
*G01N 21/85* (2006.01)
*G01J 3/02* (2006.01)
*G02B 7/02* (2006.01)
*G01N 21/15* (2006.01)

(52) U.S. Cl.
CPC ......... *G01N 21/8507* (2013.01); *G02B 7/023* (2013.01); *G01N 2021/152* (2013.01); *G01N 2021/8592* (2013.01); *G01N 2201/06113* (2013.01)

(56) References Cited

U.S. PATENT DOCUMENTS

| | | |
|---|---|---|
| 5,702,550 A | 12/1997 | Carlhoff et al. |
| 7,365,841 B2 | 4/2008 | Plessers et al. |
| 7,525,662 B2 | 4/2009 | Mannhardt et al. |
| 2009/0262345 A1 | 10/2009 | Gruber et al. |
| 2012/0038925 A1 | 2/2012 | Gahr et al. |
| 2013/0100444 A1* | 4/2013 | Chesner .................. G01J 3/443 356/318 |

FOREIGN PATENT DOCUMENTS

| | | |
|---|---|---|
| DE | 10 2004 051 310 A1 | 5/2006 |
| DE | 10 2004 051 311 A1 | 6/2006 |
| DE | 10 2008 032 532 A1 | 2/2010 |
| DE | 10 2009 028 254 A1 | 10/2010 |
| EP | 1 837 643 A2 | 3/2007 |
| GB | 2 154 315 A | 9/1985 |
| WO | WO 2007/009522 A1 | 1/2007 |

* cited by examiner

LIBS MEASUREMENT TUBE

The invention relates to a special LIBS measuring tube, which permits continuous on-line analysis, especially of elements in the VUV (vacuum UV) region, preferably sulfur, to an on-line LIBS analysis unit comprising this measuring tube, to the use thereof for qualitative and/or quantitative on-line determination of individual or multiple chemical elements of a material to be. analyzed, especially bulk substance, in particular raw, intermediate and end products from the processing of potash and magnesium salts or of rock or evaporated salt, which is being moved in a horizontal stream past the measuring tube, as well as to a corresponding method.

Laser-induced plasma spectroscopy (LIPS), also known as laser-induced breakdown spectroscopy (LIBS), represents a rapid and contactless measuring method for elemental analysis of solid, liquid or gaseous substances under normal ambient conditions without special sample preparation.

Hereinafter the abbreviation "LIBS" will be used. LIBS is a type of atomic emission spectroscopy that uses a high-energy laser pulse as the excitation source. The laser is focused on a material to be analyzed. If the laser intensity is then above a particular limit value, the material volatilizes, typically in the nanogram to microgram range. Because of the further light absorption from the energy-rich laser pulse, the micro-cloud produced is heated to high temperatures of typically above 10,000° C., resulting in a microplasma at the sample surface, i.e. a gaseous mixture of ions, electrons and excited neutral atoms. The excited atoms and ions in the plasma emit a characteristic spectrum, also known as the "fingerprint emission spectrum" which, via a rapid spectroscopic analysis, permits not only a qualitative but also, depending on the evaluation method, even a quantitative analysis of the elemental composition of the material to be analyzed. With the LIBS technique it is possible in principle to detect all elements of the periodic system, provided their element-specific emission spectrum is known.

The LIBS technique is in principle limited only by the laser power, by interferences such as peak absorption and/or peak overlapping, for example, as well as by the sensitivity and wavelength region of the detector. In practice, the detection limits depend on the plasma excitation temperature, the light-collecting window and the line intensity of the transition being observed.

For data recording it is typical to wait until thermodynamic equilibrium has been established in the plasma and the plasma temperatures are in the range of 5,000 to 20,000° C. At the high temperatures in the initial phase of the plasma, the vaporized material dissociates into excited ionic and atomic species. During this period the plasma emits a continuum of radiation, which cannot be meaningfully analyzed. Within a very short time the plasma expands with supersonic speed and cools. At that moment the characteristic atomic emission lines of the individual elements can be observed and analyzed. The time interval between the emission of the continuum radiation and the characteristic radiation is on the order of magnitude of 10 µs, and so the detector must be appropriately clocked.

A typical LIBS spectrum comprises an Nd:YAG laser and a spectrometer with a broad spectral range and a high sensitivity, a rapid response rate and a time-controlled detector. The LIBS system is interfaced with a computer, which is able to process and evaluate the recorded measured data.

The Nd:YAG laser generates pulsed laser radiation with a wavelength of 1064 nm, wherein power densities capable of exceeding 1 $GW/cm^2$ at the focusing point may be attained for pulse durations in the range of 10 ns. Other lasers that may be used for LIBS applications are eximer lasers, which generate energy in the visible and UV region of the spectrum.

The spectrometer used for analysis is in principle constructed either from a monochromator (with scanning operation) or a polychromator (without scanning operation) and a photomultiplier or CCD detector. A frequently used monochromator is the Czerny-Turner type. Frequently used polychromators are those of the echelle type or of the Paschen-Runge configuration. Even the monochromator of the Czerny-Turner detector type may be used to disperse the radiation onto a CCD, so that a polychromator results. The polychromator spectrometer is the type most frequently used in LIBS applications, since it permits simultaneous recording of the entire wavelength range of interest.

With the various available spectrometer configurations, it is possible to state briefly that, by analogy with an ICP spectrometer, an overall wavelength region from approximately 170 nm (deep ultraviolet) to approximately 1100 nm (near infrared), corresponding to the approximate sensitivity range of a CCD detector, can be measured. In contrast to the use of an ICP spectrometer, however, mainly spectrometer configurations that are sensitive for a particular wavelength range and that do not cover the above-mentioned overall wavelength range are used as a rule, for reasons of space requirements, for a LIBS measurement setup.

All elements have emission lines within this wavelength range. Depending on the quality of the measuring device, it may be possible to resolve even adjacent spectral emission lines. The selectivity can be increased by suppressing interferences.

In addition to the spectrometer and to the detector, a delay generator is used to delay the response time of the detector, so that any variation of the spectrum in time can be resolved.

Since only very small amounts of material to be analyzed are consumed during the LIBS measurement, the technique is regarded as non-destructive or minimally destructive. By repeated discharge of the laser onto the same position in the material, it is possible to generate depth profiles of a material to be investigated. For this purpose it is also possible to remove surface contaminants from the material before the actual measurement.

The LIBS technique is a purely optical method, and so only an optical access to the material to be investigated is needed. If glass-fiber optics are used, the radiation source and the analysis unit can therefore be spatially separated from the material to be investigated.

The advantages of the LIBS method lie in the speed and absence of contact, in the slight removal of material from the sample and in the fact that practically no sample preparation is required.

Multiple linear regression, principal-component analysis (PCA-LIBS), PCA-LIBS in a neuronal network or calibration-free techniques (CF-LIBS) are frequently used as evaluation methods.

The implementation of laser emission spectroscopy on moving objects is known in itself. DE A 10 2008 032 532 describes a method and a device for preparatory laser ablation of material that permits sample preparation by material removal before the actual laser emission spectroscopy.

On the industrial scale, LIBS has frequently been used heretofore for analysis of recycling metal.

For the manufacture of high-purity salt (NaCl in pharmaceutical grade, i.e. according to Ph. Eur.), the sulfate content is one of the most important quality parameters. According to the European Pharmacopoeia (compendium of drug information), the limit value is 200 ppm sulfate in pharmaceutical-grade evaporated salt.

As an example, the sulfate content is determined turbidimetrically off-line. Approximately one hour elapses from sampling to availability of the associated laboratory measured value, and so it is not possible to react quickly enough if the limit value for sulfate is exceeded. If an even lower limit value defined in-house for sulfate is exceeded, the sampling frequency is typically increased from several hours to one hour, until the sulfate content again decreases below the in-house limit value. The time delay between sampling and availability of the measured value is a disadvantage.

The object of the present invention is therefore to provide an analysis method and an analysis device with which the composition and in particular the sulfur or sulfate content can be determined under an inert-gas atmosphere with a shorter time delay, in particular for raw, intermediate and end products from the processing of potash and magnesium salts or of rock or evaporated salt, for example of high-purity salt. Preferably an on-line real-time analysis should be possible. At the same time, the analysis should be possible in simple manner in a material to be analyzed, especially bulk substance, in particular raw, intermediate and end products from the processing of potash and magnesium salts or of rock or evaporated salt.

In this case, the analysis should be possible in simple manner in a material to be analyzed that is moving in a horizontal stream, for example in a salt, that is being moved uniformly with a conveyor belt.

A further object of the present invention is to provide a device that in combination with an optics module suitable for LIBS measurements permits an analysis of the composition, in particular of raw, intermediate and end products from the processing of potash and magnesium salts or of rock or evaporated salt, for example of high-purity salt, with a shorter time delay. Preferably on-line analysis should be possible. In this case, the analysis should be possible in simple manner in a material to be analyzed, especially bulk substance, in particular raw, intermediate and end products from the processing of potash and magnesium salts or of rock or evaporated salt, wherein the material to be analyzed is being moved in a horizontal stream.

The object is achieved according to the invention by a special LIBS measuring-tube focusing unit, also referred to hereinafter (for short) as measuring tube, for dipping vertically into a material to be analyzed that is moving in a horizontal stream, especially bulk substance, in particular raw, intermediate and end products from the processing of potash and magnesium salts or of rock or evaporated salt, characterized in that
  the measuring tube extends vertically, is hollow inside and is open at least at the lower end, so that a bottom edge is formed at the lower end,
  at the upper end, the measuring tube has an inlet for coupling in a laser beam and an outlet for coupling out an emission spectrum,
  the measuring tube is constructed such that, in the measuring tube, the laser beam is focused on the material to be analyzed in such a way that a plasma of the material to be analyzed is generated inside the measuring tube by the laser beam without the occurrence of any additional scattering or deflection and the emission spectrum of the material to be analyzed passes through the interior of the measuring tube to the outlet, where it is coupled out,
  scrapers disposed to be displaced vertically against the focusing tube bear annularly on the inside and outside focusing-tube wall, preferably at the same vertical height on the focusing tube, so that material to be analyzed that is clinging to the inside and outside of the focusing tube can be scraped off by a relative movement of the focusing tube against the scrapers in the lower region.

The material to be analyzed is preferably raw, intermediate and end products from the processing of potash and magnesium salts or of rock or evaporated salt. The salt can be obtained by a chemical reaction.

For this purpose the measuring tube is preferably adapted to on-line LIBS analysis of sulfur or sulfate in raw, intermediate and end products from the processing of potash and magnesium salts or of rock or evaporated salt.

The object is additionally achieved by an on-line LIBS analysis unit comprising
  a LIBS measuring tube as described in the foregoing,
  a laser-beam source,
  a spectrometer unit for recording the LIBS emission spectrum, with analysis optics for the spectral region of 170-590 nm and if necessary for detection in the IR region,
  optical structural elements for coupling the laser beam into the measuring tube and for coupling the emission spectrum out of the measuring tube (part of the focusing optics),
  control electronics for operation of the laser-beam source and detector unit as well as for measured-value recording,
  a preferably pneumatic drive unit for automated relative movement of the focusing tube against the scrapers,
  a device for injecting inert gas into the measuring tube, which only then makes it possible to detect the spectra of elements that emit in the VUV region, preferably of sulfur.

The object is additionally achieved by the use of such a measuring tube or of such an on-line LIBS analysis unit for qualitative and/or quantitative on-line determination of individual or several chemical elements of a material to be analyzed, especially bulk substance, in particular raw, intermediate and end products from the processing of potash and magnesium salts or of rock or evaporated salt, which is being moved in a horizontal stream past the measuring tube.

The object is additionally achieved by a method for qualitative and/or quantitative on-line determination of individual or multiple chemical elements of a material to be analyzed, especially bulk substance, in particular raw, intermediate and end products from the processing of potash and magnesium salts or of rock or evaporated salt, which is moving in a horizontal stream, with an on-line LIBS analysis unit as described in the foregoing, in which the LIBS measuring tube is dipped vertically in a horizontal stream of moving material to be analyzed, especially bulk substance, in particular raw, intermediate and end products from the processing of potash and magnesium salts or of rock or evaporated salt, a laser beam is generated by means of the laser-beam source and focused on the material to be analyzed in the measuring tube, so that a plasma generated by the laser beam from the material to be analyzed, especially bulk substance, in particular raw, intermediate and end products from the processing of potash and magnesium salts or of rock or evaporated salt, is formed inside the measuring tube and the emission spectrum of the material to be analyzed passes through the interior of the measuring tube to the outlet, where it is coupled out to the detector unit and measured-value recording takes place there.

It has been found that determination of principal and/or trace elements in salts, in particular pharmaceutical-grade evaporated salt and potash salt, is possible by means of LIBS provided an inventive measuring tube is used, wherein the salts are moved in a horizontal stream, typically on a conveyor belt.

The inventive LIBS measuring tube and the on-line LIBS analysis unit permit the determination of principal and/or trace elements in salts, for example potash and pharmaceutical grade evaporated salt, with high accuracy and reliability in on-line real-time operation. The on-line analysis of principal, minor and trace elements in raw materials, intermediate products and end products of the potash and rock salt industry is possible. Even the on-line determination of elements emitting in the UV region, such as sulfur, is possible under a shielding-gas atmosphere. In particular, the analysis of K, Na, Ca, Mg and S is possible for salts. For this purpose, the determination of S typically must be carried out under an inert-gas atmosphere (as is also the case, for example, for C and P).

The on-line determination of sulfur in the trace range by means of LIBS can be accomplished with sufficient accuracy preferably in the UV or VUV wavelength range. Because of the absorption of the element-specific wavelengths by air, this determination must be carried out preferably under an inert-gas atmosphere.

According to the invention, nitrogen or argon is preferably considered as inert gases.

By virtue of the determination of sulfur, the sulfate content of the salt, for example of pharmaceutical-grade evaporated salt, is therefore accessible.

The inventive method permits quasi-real-time process control and process adaptation or process optimization in the event of deviation from limit values. Such a measuring system can be installed on an application-specific basis and optionally with the use of shielding gas, for example above a conveyor belt or turntable. The analysis is then carried out continuously on moving sample material. The analysis results are available on-line and therefore can be transmitted to the respective process control system. According to the invention, a LIBS measuring tube is described that is provided for dipping vertically into a material to be analyzed, moving in a horizontal stream. According to the invention, this term "vertical" encompasses deviations from the vertical by ±44°, preferably ±22°, in particular ±11°, especially ±5°.

According to the invention, the term "horizontal" comprises deviations from the horizontal of ±44°, preferably ±22°, in particular ±11°, especially ±5°.

The arrangement of the measuring tube and of the material to be analyzed, moving in the stream, is preferably such that a uniform stream of the material to be analyzed is achieved and dipping of the lower part of the measuring tube into the stream of material to be analyzed is possible, in order to undertake, at the dipping point, an analysis of the material to be analyzed, for example in the VUV region, such as sulfur.

Particularly preferably, vertical dipping of the measuring tube takes place into a horizontal stream of the material to be analyzed, i.e. an angle of 90°±20°, preferably 10°, in particular ±5° exists between the two directions.

The measuring tube extends vertically in the sense mentioned hereinabove. It has an extent in the vertical direction in order to permit a distance between the inlet for coupling in the laser beam and the outlet for coupling out the emission spectrum and the sample surface, i.e. the surface of the material to be analyzed. Preferably the distance of the last optical component of the measuring system to the average material surface is at least 50 mm, preferably at least 100 mm, in particular at least 200 mm. Typically the distance of the last optical component of the measuring system to the average material surface may be approximately 250 mm.

The focusing tube may have any desired suitable shape. Typically it is made in tubular shape with any desired cross section. An elliptical or in particular circular cross section of the focusing tube is preferred.

By "at the upper end" a region above the middle of the measuring tube (in vertical alignment) will be understood, preferably in the upper third of the measuring tube, in particular in the upper fourth of the measuring tube. Particularly preferably, the inlet and the outlet are disposed as close as possible to the upper end of the measuring tube.

The expression "in the lower region", as used according to the invention in the context of scraping of the focusing tube, denotes a region below the middle of the measuring tube (viewed in vertical direction), preferably the lower third, particularly preferably the lower fourth of the measuring tube.

Plasma generation and collection of the emission spectrum take place inside the measuring tube, preferably—for measurements of elements under a shielding-gas atmosphere—when the lower end of the measuring tube is dipped into the material to be analyzed. To perform the measurement, the laser beam is focused on the material to be analyzed or on the surface thereof. As an example, this may be accomplished by means of an autofocusing device.

The material to be analyzed, moving in the horizontal stream, may preferably exist as a solid, gas, gel, sol, dispersion, liquid or mixture thereof, especially as bulk substance, in particular as a raw, intermediate and end product from the processing of potash and magnesium salts or rock and evaporated salt. If the material to be analyzed is not inherently free-flowing, it preferably exists in such a finely divided form that it is able to lie on a conveyor belt or is pourable. Particularly preferably, the material to be analyzed is a solid, especially a bulk substance, in particular a raw, intermediate and end product from the processing of potash and magnesium salts or rock and evaporated salt, which in particular exists in particulate form. The mean particle size then lies preferably in the range of 0.5 to 10 mm, particularly preferably 2 to 4 mm, in particular 0.5 to 1 mm.

Due to the dipping of the measuring tube into the stream of material to be analyzed, in particular bulk substance, in particular as a raw, intermediate and end product from the processing of potash and magnesium salts or rock and evaporated salt, clinging masses of the material to be analyzed may be formed on the measuring tube, especially in bulk substances with a moisture content >1%. Typically this occurs at points in the region of dipping of the measuring tube, i.e. at its lower, inside end. Since a wave of the material or bulk substance may form at the inflow side when the lower part of the measuring tube is dipped in the material to be analyzed, clinging/caked masses due to steady accretion may be formed above the dipping position, in particular for bulk substances from the processing of potash and magnesium salt or rock or evaporated salt with a moisture content >1%.

The clinging masses may impair the LIBS analyses by the fact that clinging/caked masses are formed increasingly at the lower, inside end of the measuring tube and the clinging material greatly minimizes or even negates the accuracy of analysis of the freshly arriving material to be analyzed, especially bulk substance, in particular raw, intermediate and end products from the processing of potash and magnesium salts or rock or evaporated salt.

Therefore the measuring tube is provided with annular scrapers on the inside and outside tube wall. These are pushed vertically against the focusing tube, so that material to be analyzed, clinging to the inside and outside of the measuring tube in the lower region, can be scraped therefrom by a relative movement of the focusing tube against the scrapers. Scraping then takes place in particular in the region of the focusing tube over which the scrapers are moved.

It is possible according to the invention to move the scrapers over a fixed tube. However, it is preferable to provide that the inside and outside scrapers do not move and to shift the focusing tube up and down between the scrapers in order to achieve scraping in this way.

The scrapers bear annularly on the inside and outside focusing-tube wall. The vertical height of these scrapers may be chosen to meet practical requirements. During the relative movement of the focusing tube against the scrapers, these scrape along the inside and outside wall of the focusing tube in the lower region and thus detach particles of the material to be analyzed clinging to the measuring tube. In order to ensure optional functioning of the scrapers, they are preferably disposed in such a way on the focusing tube that in measuring operation they are not dipped into the horizontal stream of the material to be analyzed. On the other hand, cleaning of the focusing tube by the relative movement is still possible even if the scrapers are dipped.

The particularly preferred movement of the focusing tube against the fixed scrapers during the scraping process makes it possible to dip the measuring tube into the still-moving stream for a new measurement, so that the salt composition respectively present at the measuring position on a conveyor belt is investigated at time intervals.

During the measurement, the measuring tube preferably dips so deeply into the material to be analyzed that the lower edge of the measuring tube dips completely into the material to be analyzed.

It has proved advantageous to chamfer the lower end of the measuring tube so that the lower edge of the measuring tube on the upstream side of the stream of material to be analyzed dips deeper into this stream than on the downstream side. Hereby an increased flow of the material to be analyzed into the measuring tube is reliably prevented, as is upward travel thereof in the measuring tube.

The scraping movement may be driven in any desired suitable way. Preferably the measuring tube is provided with a preferably pneumatic drive unit for automatic relative movement of the focusing tube against the scrapers.

It is further advantageous to provide a control and regulation unit for automation of scraping.

The scraping movement can take place at regular, variably clockable time intervals during the LIBS measurements in on-line operation.

Thus LIBS measurements can be carried out in on-line operation, wherein material to be analyzed, clinging to the measuring tube, is scraped off therefrom, preferably automatically, by a relative movement of the focusing tube against the scrapers during the LIBS measurements.

According to a preferred embodiment, the measuring tube has an inlet for injection of inert gas. Hereby it is possible to work with the LIBS analysis technique under inert gas and, in fact, to do so in on-line operation. This is necessary, for example, for the determination of sulfur in the UV region.

In this connection it is preferable to fill the entire measuring tube with inert gas for these measurements. To ensure that not too much inert gas escapes, it is additionally possible to dip the bottom edge of the measuring tube completely into the material to be analyzed. If a sufficient stream of inert gas is ensured, however, the bottom edge of the measuring tube may even be disposed partly or completely above the material to be analyzed, provided ingress of air or atmospheric oxygen into the region between the material surface and the upper end of the measuring tube (inside) is prevented.

Since the height of the bulk substance of the moving stream of material to be analyzed may vary, it is advantageous to provide, in the on-line LIBS analysis unit, an autofocusing system, which functions to adapt the measuring distance to the material to be analyzed, The inventive measuring tube, the inventive analysis unit and the inventive method may be applied to any desired suitable materials to be analyzed. Preferably the material to be analyzed is a solid, a gas, a gel, a sol, a dispersion, a liquid or mixtures thereof. Preferably the material to be analyzed is a salt, in particular a raw, intermediate or end product from the processing of potash and magnesium salts or rock or evaporated salt.

In particular, the sulfur content of a salt is determined in on-line operation under an inert-gas atmosphere with the inventive method.

According to the invention, the LIBS analysis may be carried out as specified in the introduction to the description. Preferred designs of the inventive measuring tube and of the analysis unit are indicated hereinafter.

The measuring system is preferably provided with an automatic controller and is able to signal the respective current condition (such as standby, ready, measurement in progress, error) to the higher level process control system. In addition, self-tests on the functional readiness are performed.

The measuring system automatically performs measurements on moving material, for example on a conveyor belt.

During testing of the material surface, the material surface is exposed to laser radiation, which induces emission of plasma radiation. This is detected in an optical analysis system and evaluated with the integrated signaling electronics and control software.

The measuring system is designed to transmit the measured results to a higher-level process control system.

Recalibration and monitoring of the testing equipment are carried out at defined time intervals.

All measured values, test results and information about the system condition are recorded.

The laser-based on-line measuring system and the continuous analysis permit quasi-real-time process control and process optimization.

The optical analysis system preferably permits an analysis in the spectral region from 170 to 590 nm and if necessary also in the IR region. Using the LIBS technique, the measuring system continuously tests the material that is present, for example on a conveyor belt. The measured elemental contents are available to the system user on-line.

The measuring system consists of the housing, laser-beam source, optics including the measuring tube, autofocusing system, control electronics and software subassemblies as well as protective devices.

The housing functions to accommodate all optical and electronic components as well as the media and user interfaces. The housings, including the cable entry, are preferably water-jet-proof, dust-tight, laser-safe and temperature-stabilized.

The measuring tube protects the optics from contamination and beyond this permits determination of elements under an inert-gas atmosphere in the VUV region. The measuring tube is a component of the focusing optics and is flanged onto the optics module, which among other components consists of laser, optics and spectrometer.

As the laser, a pulsed Nd:YAG laser-beam source (laser class 4) with a mean optical power of at most 30 W is used for excitation of the element-specific optical emission. An autofocusing system is used for adaptation of the measuring distance, for example to different belt coverages. It consists of distance sensors and positioning units, which ensure focusing of the laser beam on the material surface.

The control electronics are used for sequence control.

Control software is likewise used for sequence control, interfacing to a process control system, control and operation of the measuring system, evaluation of the measured values, calibration, recalibration, test-equipment monitoring, as the interface to the process control computer, as the record-keeping function, set-up operation and for remote maintenance.

In practice, preferably protective devices are provided that function as protection from laser radiation and moving parts by interlock circuits, safety catches, etc.

It is possible to guide the pulsed laser beam such that its motion is synchronized with a preselected measurement point from the moving material to be analyzed in such a way that consecutive laser pulses or laser bursts can be applied several times in succession to the same sample location. Hereby depth-stepped analysis of the material is possible on the one hand and clinging masses on the surface can be removed.

In this way it is possible, during use of a method and a device, the exact description of which is presented in DE A 10 2008 032 532, to carry out preparatory laser ablation of material by means of a pulsed laser beam, even on moving objects to be measured.

It is also possible in principle to carry out measurements at several measurement locations inside the measuring tube. A corresponding method procedure is described, for example, in DE A 10 2004 051 310.

Furthermore, it is possible to combine the LIBS measurement with a laser-induced fluorescence measurement (LIS measurement), as is described, for example, in DE A 10 2004 051 311.

Furthermore, it is possible to use double-pulse laser systems, which may exist in orthogonal or perpendicular configuration. For example, in this way signal amplification can be achieved that otherwise would be possible only by working at reduced pressures.

The present invention will be explained in more detail by the following example.

EXAMPLE 1

Figure 1:
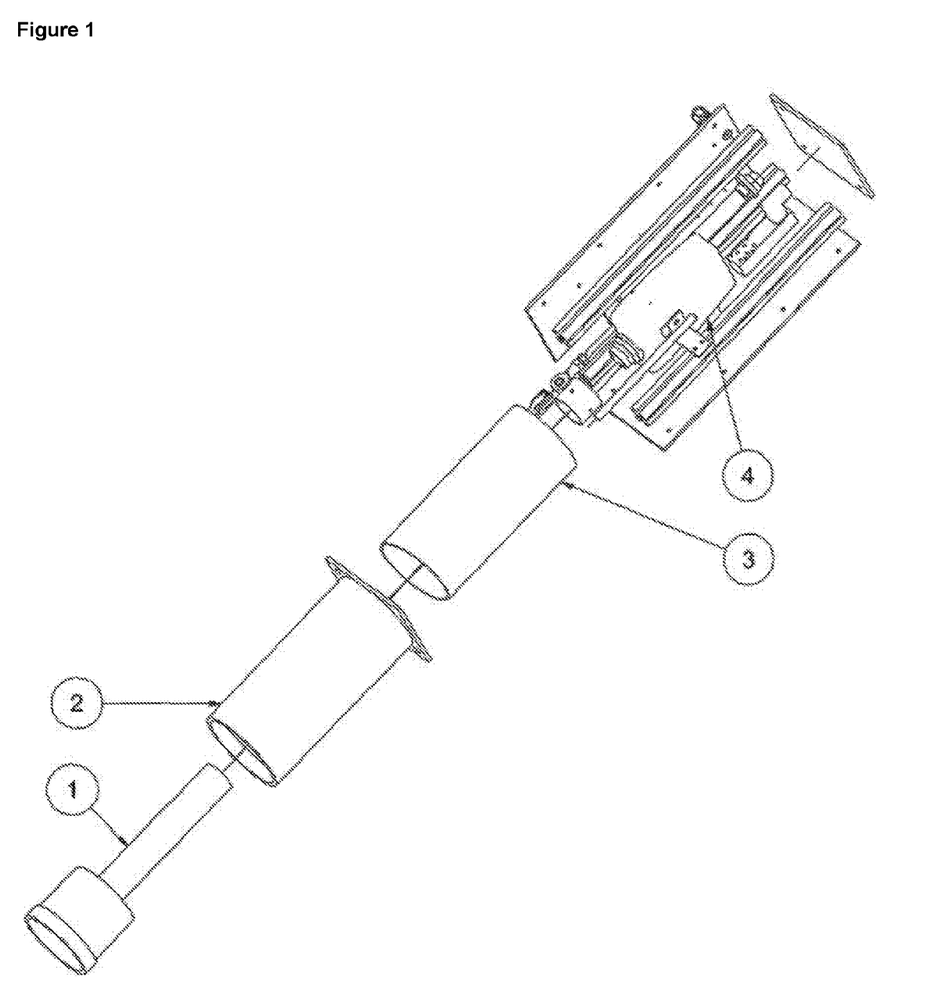
Figure 2:
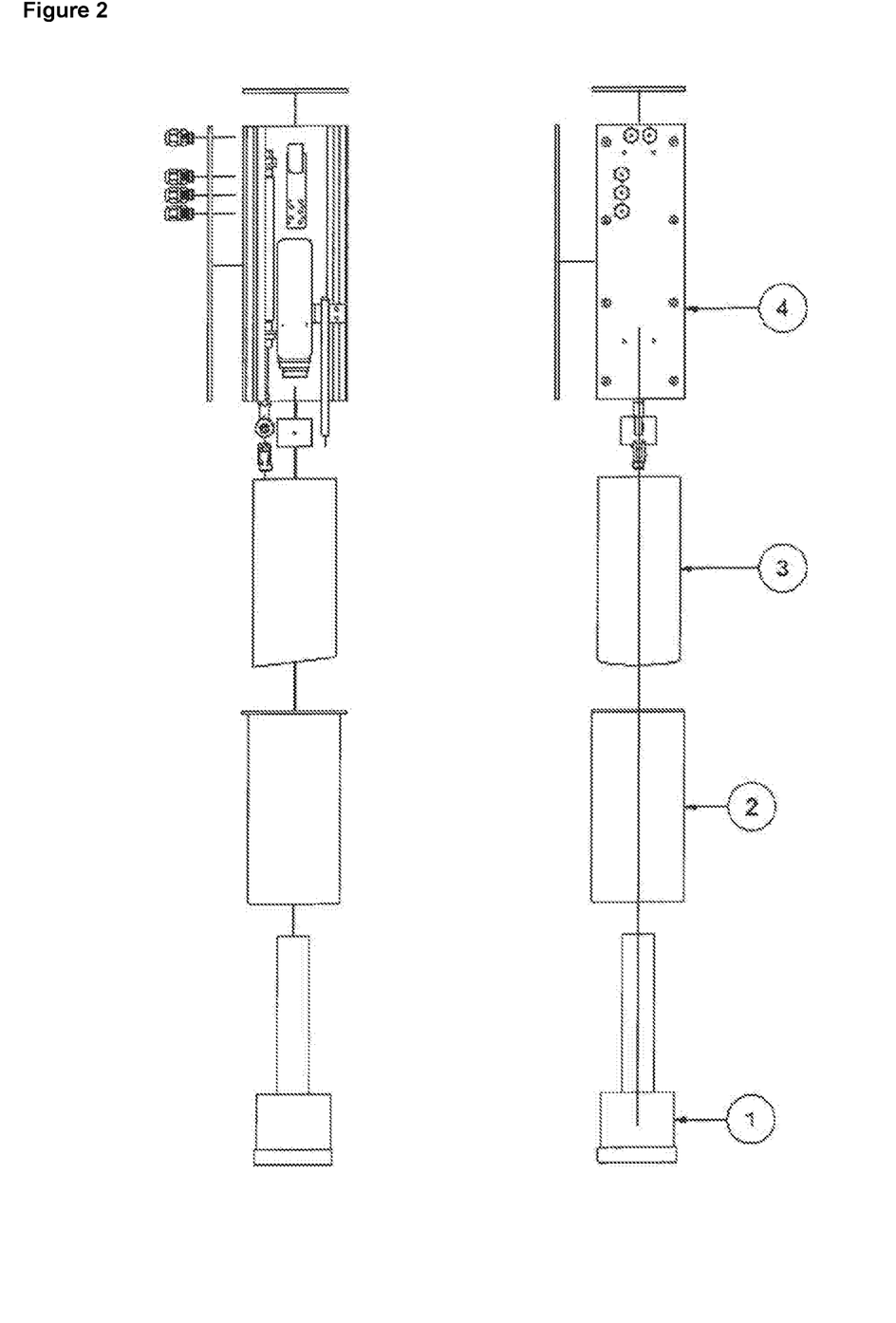

The measuring tube was developed with the basic idea that it consists of a double-tube system, in which a focusing tube is intended to be operated in real on-line operation for the needed inert-gas atmosphere as close as possible above the salt surface, but with as little surface contact as possible by means of autofocus, or alternatively is intended to be dipped into the salt. To the extent that contact takes place between focusing tube and salt, a double tube with manual inner-tube scraper (in on-line operation, scraping can take place automatically in a clocked sequence) was made for the basic tests (manual measuring tube). The outer tube constituted the outer scraper. In the inner tube (which corresponds to the focusing tube), a further tube was provided as the inner scraper. FIGS. 1 and 2 show the schematic structure of the automated measuring tube, made on the basis of the manual measuring tube, as an exploded diagram with the following reference symbols:

1 Inner scraper
2 Outer scraper
3 Focusing tube
4 Control and evaluation logic.

Figure 3:
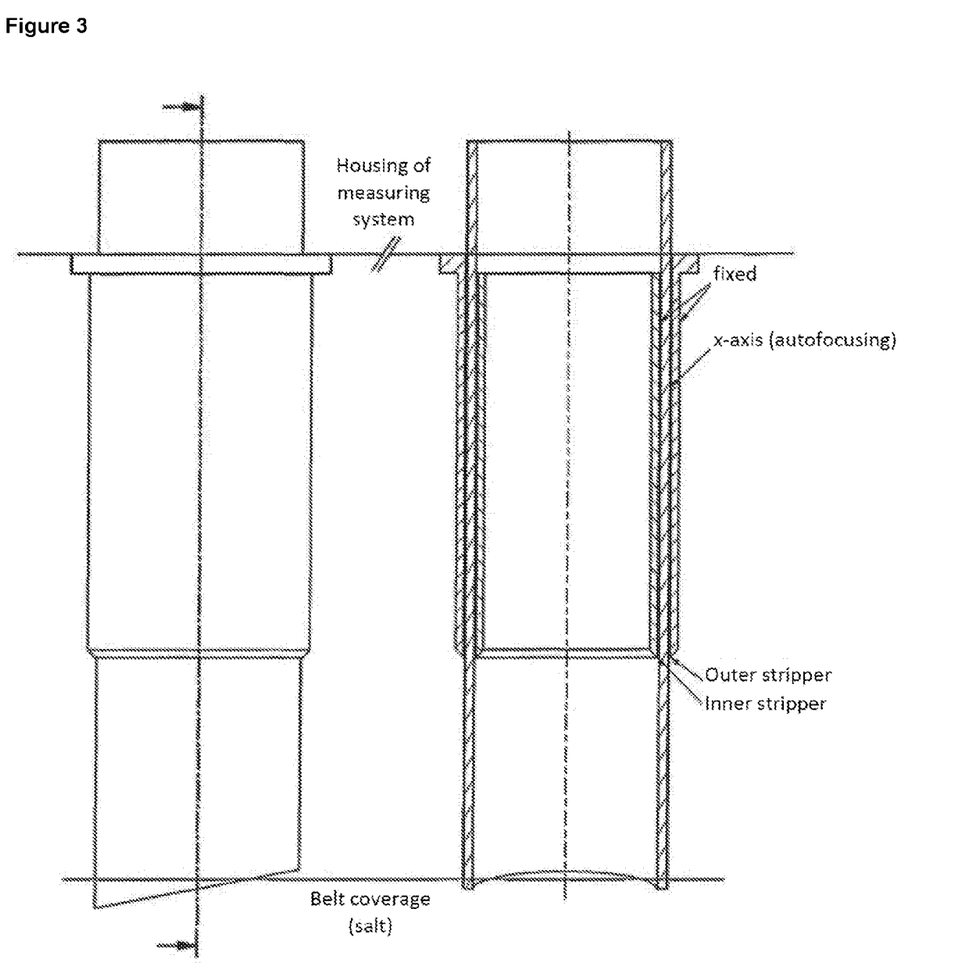

FIG. 3 shows a top view and cross-sectional view of the manual measuring tube with scrapers.

The manual measuring tube was installed vertically above a horizontal conveyor belt. Evaporated salt was being conveyed on the conveyor belt.

The manual measuring tube was installed in such a way at first that the extended focusing tube was located minimally above the salt surface. Since the belt coverage was not constant, however, direct contact between the focusing tube and the salt occurred rapidly. Thereupon the focusing tube was dipped even deeper, in order to expose it to maximum conditions and to leave it intentionally in full contact with the salt.

Hereby it was the intention to investigate whether salt backups develop in the inner tube and whether outer caked masses on the inner tube can be removed effectively by the provided scraper mechanism. For this purpose, several contact times between the focusing tube and the salt were tested before manual actuation of the scraper mechanism.

For this purpose, several time intervals (repeatedly 1 minute, repeatedly 5 minutes, 1 hour, 1.5 hours) were tested between the actuations of the scraper mechanism.

Observations after Repeated 1-Minute Contact Between Focusing Tube and Salt (Dipping Time):

The outer part of the focusing tube, which was in direct contact with the product stream, exhibited the first salt deposits, although no caked masses and salt backups were formed in the inner tube and on the inner-tube edge. After actuation of the scraper mechanism, it was possible to remove the outer deposits without problems.

Observations after Repeated 5-Minute Contact Between Focusing Tube and Salt (Dipping Time):

The outer part of the focusing tube in contact with the product stream exhibited new salt deposits. After this time, the first small caked salt masses were also visible on the inner-tube edge. However, no new caked masses and salt backups were formed directly in the inner tube. After actuation of the scraper mechanism, it was also possible in this case to remove the outer deposits as well as the deposits on the inner-tube edge effectively.

Observations During a Disturbance of Salt Production that Occurred by Coincidence:

During the test phase a blockage of salt production developed, and so temporarily no evaporated salt was being conveyed on the belt.

When the blockage was cleared, large irregularities were observed in the belt coverage. Nevertheless, the manual measuring tube was intentionally not altered in its height at that time, but was exposed to these more difficult conditions, in order to test its behavior under such a production condition. In this case it was possible to observe that at times the focusing tube was dipped into the product stream up to the height of the outer scraper.

Besides the irregular belt coverage, some large salt nodules were also present on the conveyor belt, although they were deflected without problems at the measuring tube and conveyed further alongside it on the belt without dropping from the wet-salt belt.

After dipping deeply into the product stream and making contact with salt nodules, the measuring tube had new caked masses on the outside edge and on the focusing tube. However, it was again possible to remove these without problems by actuation of the scraper mechanism.

Observations after 1-Hour and 1.5-Hour Contact Between Focusing Tube and Salt:

In each case the outer part of the focusing tube in contact with the product stream exhibited larger salt deposits, and after these contact times caked salt masses were also visible on the inner-tube edge. However, these were not any larger than during a contact time of 5 minutes, presumably since edge caked masses on the edge were invariably somewhat loosened again by the moving conveyor process. Caked masses and salt backups were not observed in the inner tube after 1 hour or even after 1.5 hours. After actuation of the scraper mechanism, it was possible even after these longer contact times to remove the outer deposits as well as the deposits on the inner-tube edge. After the measuring tube was dismantled, it was likewise apparent that no caked masses were present on the chamfered rear part of the focusing tube. Thus the front part of the focusing tube had functioned as a kind of plow and the chamfered rear geometry of the tube had presumably prevented salt backups in the inner part of the tube.

EXAMPLE 2

When an automated measuring tube according to FIG. 1 was used, advantageous measuring behavior, comparable with that of Example 1, was found in automated operation.

The invention claimed is:

1. A LIBS measuring tube for dipping vertically into a material to be analyzed that is moving in a horizontal stream wherein
   the measuring tube extends vertically, is hollow inside and is open at least at a lower end, so that a bottom edge is formed at the lower end,
   at an upper end, the measuring tube has an inlet for coupling in a laser beam and an outlet for coupling out an emission spectrum,
   the measuring tube is constructed such that, in the measuring tube, the laser beam is focused on the material in such a way that a plasma of the material is generated inside the measuring tube by the laser beam without occurrence of any additional scattering or deflection and an emission spectrum of the material passes through an interior of the measuring tube to the outlet, where it is coupled out, and
   scrapers disposed to be displaced vertically against a focusing tube bear annularly on an inside wall and an outside wall of the focusing-tube, so that material clinging to the inside and outside of the focusing tube is scraped off by a relative movement of the focusing tube against the scrapers in a lower region.

2. The measuring tube according to claim 1, which has an inlet for injection of inert gas, which permits detection of spectra of elements that emit in a VUV region.

3. The measuring tube according to claim 1, wherein the scrapers bear on the focusing tube in such a way that during measuring operation the scrapers do not dip into the horizontal stream of the material.

4. The measuring tube according to claim 1, wherein the focusing tube and the scrapers are tubular.

5. The measuring tube according to claim 1, wherein the focusing tube and the scrapers have a circular cross section.

6. The measuring tube according to claim 1, wherein the lower end of the measuring tube is chamfered, so that a lower edge of the measuring tube on an upstream side of the stream of the material dips deeper into this stream than on a downstream side.

7. The measuring tube according to claim 1, which is provided with a pneumatic drive unit for automatic relative movement of the focusing tube against the scrapers.

8. An on-line LIBS analysis unit, comprising
   the LIBS measuring tube according to claim 1,
   a laser-beam source,
   a spectrometer unit for recording a LIBS emission spectrum, with analysis optics for a spectral region of 170-590 nm and for detection in an IR region,
   an optical structural element for coupling the laser beam into the measuring tube and for coupling the emission spectrum out of the measuring tube,
   a control electronic for operation of the laser-beam source and detector unit as well as for measured-value recording,
   a pneumatic drive unit for automated relative movement of the focusing tube against the scrapers, and
   a device for injecting inert gas into the measuring tube, which permits detections of spectra of elements that emit in a VUV region.

9. The analysis unit according to claim 8, further comprising an autofocusing system for adapting measuring distance to the material.

10. The analysis unit according to claim 8, further comprising a control and regulation unit for automation of scraping by a pneumatic drive unit for automated relative movement of the focusing tube against the scrapers.

11. A method for qualitative and/or quantitative on-line determination of individual or multiple chemical elements of a material, the method comprising:
    employing the measuring tube according to claim 1,
    wherein the material is moved in a horizontal stream past the measuring tube.

12. The method according to claim 11, wherein the material is a solid, a gas, a gel, a sol, a dispersion, a liquid or a mixture thereof.

13. The method according to claim 11, wherein the material is a salt.

14. The method according to claim 13, wherein a sulfur content of the salt is determined in on-line operation under an inert-gas atmosphere.

15. A method for qualitative and/or quantitative on-line determination of individual or multiple chemical elements of a material moving in a horizontal stream with the on-line LIBS analysis unit according to claim 8, the method comprising:
    dipping the LIBS measuring tube vertically in the horizontal stream of the material,
    generating a LIBS laser beam via the laser-beam source, and
    focusing the LIBS laser beam on the material in the measuring tube, so that a plasma generated by the laser beam from the material is formed inside the measuring tube and an emission spectrum of the material passes through an interior of the measuring tube to the outlet, where it is coupled out to the detector unit and measured-value recording takes place.

16. The method according to claim 15, further comprising:
   carrying out a LIBS measurement in succession in on-line operation,
   wherein the material which clings to the measuring tube is scraped off therefrom by a relative movement of the focusing tube against the scrapers during the LIB S measurements.

17. The method according to claim 16, wherein the LIBS measurement is carried out under an inert-gas atmosphere, by injecting inert gas into the measuring tube.

18. The method according to claim 15, wherein the material is a solid, a gas, a gel, a sol, a dispersion, a liquid or a mixture thereof.

19. The method according to claim 15, wherein the material is a salt.

20. The method according to claim 19, wherein a sulfur content of the salt is determined in on-line operation under an inert-gas atmosphere.

* * * * *